(12) United States Patent
Morris et al.

(10) Patent No.: US 7,465,315 B2
(45) Date of Patent: *Dec. 16, 2008

(54) PORTAL DESIGN FOR STENT FOR TREATING BIFURCATED VESSELS

(75) Inventors: Grayson Morris, San Francisco, CA (US); Rommel Lumauig, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 178 days.

This patent is subject to a terminal disclaimer.

(21) Appl. No.: 11/495,081

(22) Filed: Jul. 28, 2006

(65) Prior Publication Data

US 2006/0265050 A1    Nov. 23, 2006

(51) Int. Cl.
*A61F 2/06* (2006.01)

(52) U.S. Cl. .................................. 623/1.15; 623/1.35

(58) Field of Classification Search ........ 623/1.11–1.36
See application file for complete search history.

(56) References Cited

U.S. PATENT DOCUMENTS

| | | | |
|---|---|---|---|
| 2,978,787 A | 4/1961 | Leibig |
| 2,990,605 A | 7/1961 | Densyk |
| 3,029,819 A | 4/1962 | Starks |
| 3,096,560 A | 7/1963 | Liebig |
| 3,142,067 A | 7/1964 | Liebig |
| 3,657,744 A | 4/1972 | Ersek |
| 3,908,662 A | 9/1975 | Razgulov et al. |
| 3,945,052 A | 3/1976 | Liebig |

(Continued)

FOREIGN PATENT DOCUMENTS

DE    91 02 312 U1    6/1992

(Continued)

OTHER PUBLICATIONS

Lawrence, David D., Jr., M.D., et al. Percutaneous Endovascular Graft: Experimental Evaluation, *Radiology*, vol. 163, No. 2, pp. 357-360 (1987).

(Continued)

*Primary Examiner*—Suzette J Gherbi
(74) *Attorney, Agent, or Firm*—Fulwider Patton LLP

(57) ABSTRACT

A stent pattern includes an improved portal region for repairing a main vessel and a side branch vessel forming a bifurcation. More particularly, the stent has rings aligned along a common longitudinal axis that are connected by links, where the stent has a proximal section, a distal section, and a central section (portal region). The number of rings and the expanded diameter of the sections are varied to create a "trap door" capable of expanding to a slightly larger diameter than the proximal section and the distal section of the stent. The configuration of the stent pattern of the portal region prevents the occurrence of portal overlap of immediately adjacent rings into the portal region during stent deployment. The stent is implanted at a bifurcation so that the proximal section and the distal section are in the main vessel, and the central section contacts at least a portion of the opening to the side branch vessel. A second stent can be implanted in the side branch vessel and abut the expanded central section to provide full coverage of the bifurcated area in the main vessel and the side branch vessel.

33 Claims, 10 Drawing Sheets

U.S. PATENT DOCUMENTS

| | | | |
|---|---|---|---|
| 4,041,931 A | 8/1977 | Elliott et al. | |
| 4,047,252 A | 9/1977 | Liebig et al. | |
| 4,061,134 A | 12/1977 | Samuels et al. | |
| 4,108,161 A | 8/1978 | Samuels et al. | |
| 4,140,126 A | 2/1979 | Choudhury | |
| 4,193,137 A | 3/1980 | Heck | |
| 4,202,349 A | 5/1980 | Jones | |
| 4,214,587 A | 7/1980 | Sakura, Jr. | |
| 4,517,687 A | 5/1985 | Liebig et al. | |
| 4,560,374 A | 12/1985 | Hammerslag | |
| 4,562,596 A | 1/1986 | Kornberg | |
| 4,577,631 A | 3/1986 | Kreamer | |
| 4,617,932 A | 10/1986 | Kornberg | |
| 4,652,263 A | 3/1987 | Herweck et al. | |
| 6,159,238 A | 12/2000 | Killion | |
| 6,165,195 A | 12/2000 | Wilson et al. | |
| 6,183,509 B1 | 2/2001 | Dibie | |
| 6,203,568 B1 | 3/2001 | Lombardi et al. | |
| 6,210,429 B1 | 4/2001 | Vardi et al. | |
| 6,221,098 B1 | 4/2001 | Wilson et al. | |
| 6,254,593 B1 | 7/2001 | Wilson | |
| 6,258,116 B1 | 7/2001 | Hojeibane | |
| 6,264,682 B1 | 7/2001 | Wilson et al. | |
| 6,290,673 B1 | 9/2001 | Shanley | |
| 6,325,826 B1 | 12/2001 | Vardi | |
| 6,346,089 B1 | 2/2002 | Dibie | |
| 6,358,274 B1 | 3/2002 | Thompson | |
| 6,361,555 B1 | 3/2002 | Wilson | |
| 6,896,697 B1* | 5/2005 | Yip et al. | 623/1.15 |
| 7,090,694 B1* | 8/2006 | Morris et al. | 623/1.15 |
| 2001/0029397 A1 | 10/2001 | Thompson | |
| 2001/0037137 A1 | 11/2001 | Vardi et al. | |
| 2001/0049548 A1 | 12/2001 | Vardi et al. | |
| 2001/0056297 A1 | 12/2001 | Hojeibane | |
| 2003/0036793 A1 | 2/2003 | Richter et al. | |
| 2003/0097169 A1 | 5/2003 | Brucker et al. | |
| 2003/0125802 A1 | 7/2003 | Callol et al. | |
| 2003/0139796 A1 | 7/2003 | Sequin et al. | |
| 2003/0139803 A1 | 7/2003 | Sequin et al. | |
| 2003/0167983 A1 | 9/2003 | Lashinski et al. | |
| 2003/0195606 A1 | 10/2003 | Davidson et al. | |
| 2003/0204244 A1* | 10/2003 | Stiger | 623/1.16 |
| 2004/0039439 A1* | 2/2004 | Gomez et al. | 623/1.16 |
| 2004/0044400 A1* | 3/2004 | Cheng et al. | 623/1.16 |
| 2004/0133265 A1* | 7/2004 | Duffy | 623/1.16 |
| 2004/0133271 A1* | 7/2004 | Jang | 623/1.42 |

FOREIGN PATENT DOCUMENTS

| | | |
|---|---|---|
| EP | 0 461 791 A1 | 12/1991 |
| EP | 0 466 518 A3 | 1/1992 |
| EP | 0747 020 A2 | 12/1996 |
| EP | 0 804 907 A2 | 11/1997 |
| EP | 0 897 700 A1 | 2/1999 |
| EP | 0 904 745 A2 | 3/1999 |
| FR | 2673843 A1 | 9/1992 |
| FR | 2737969 A1 | 2/1997 |
| SU | 1217402 A | 3/1986 |
| SU | 1318235 A1 | 6/1987 |
| SU | 1389778 A2 | 4/1988 |
| SU | 1457921 A1 | 2/1989 |
| SU | 1482714 A2 | 5/1989 |
| WO | WO 95/16406 A1 | 6/1995 |
| WO | WO 95/21592 A1 | 8/1995 |
| WO | WO 96/23455 A1 | 8/1996 |
| WO | WO 96/24306 A1 | 8/1996 |
| WO | WO 96/24308 A1 | 8/1996 |
| WO | WO 96/34580 A1 | 11/1996 |
| WO | WO 97/07752 A1 | 3/1997 |
| WO | WO 97/15346 A1 | 5/1997 |
| WO | WO 97/16217 A1 | 5/1997 |
| WO | WO 97/41803 A1 | 11/1997 |
| WO | WO 97/45073 A1 | 12/1997 |
| WO | WO 98/19628 A1 | 5/1998 |
| WO | WO 98/36709 A1 | 8/1998 |
| WO | WO 99/04726 A1 | 2/1999 |
| WO | WO 00/07523 A1 | 2/2000 |
| WO | WO 01/21095 A2 | 3/2001 |
| WO | WO 02/068012 A1 | 9/2002 |

OTHER PUBLICATIONS

Yoshioka, Tesuya, et al., Self-Expanding Endovascular Graft: An Experimental Study in Dogs, *Radiology*, vol. 170, pp. 673-676 (1989).

Mirich, David, M.D., et al., Percutaneously Placed Endovascular Grafts for Aortic Aneurysms: Feasibility Study, *Radiology*, vol. 170, No. 3, Part 2, pp. 1033-1037 (1989).

Parodi, J.C., M.D., et al., Transfemoral Intraluminal Graft Implantation for Abdominal Aortic Aneurysms, *Annals of Vascular Surgery*, vol. 5, No. 6, pp. 491-499 (1991).

Chuter, Timothy A.M., et al., Transfemoral Endovascular Aortic Graft Placement, *Journal of Vascular Surgery*, pp. 185-196 (Aug. 1993).

Bard XT Carina Bifurcate Stent (Brochure) (Undated).

* cited by examiner

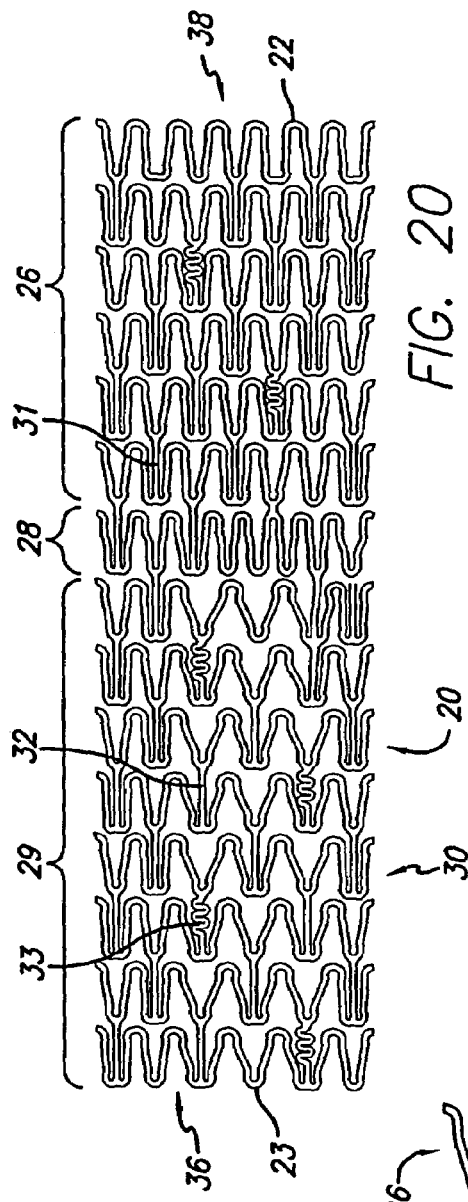
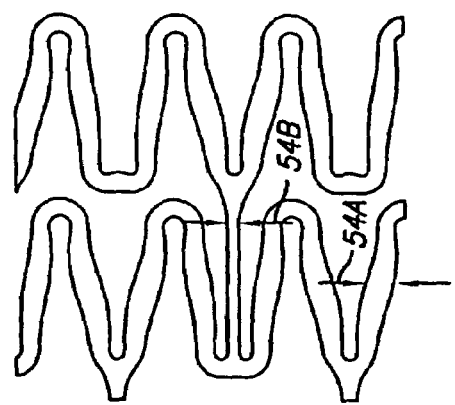
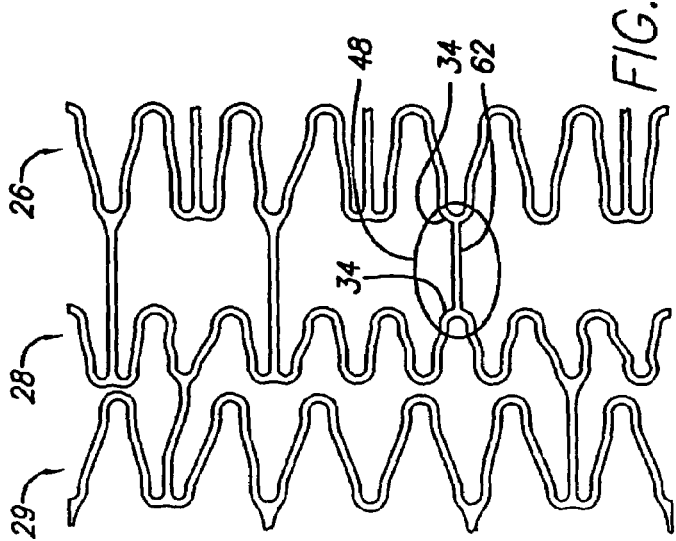

PORTAL DESIGN FOR STENT FOR TREATING BIFURCATED VESSELS

BACKGROUND OF THE INVENTION

The invention relates to vascular repair devices, and, in particular, intravascular stents for repairing bifurcations, blood vessels that are diseased. Stents are particularly useful in the treatment of atherosclerotic stenosis in arteries and blood vessels. More particularly, the invention concerns improved stent patterns for a portal region on a side branch access stent to prevent the occurrence of portal overlap during deployment of the stent. The invention further provides a method of making a stent for repairing a bifurcated vessel.

Stents conventionally repair blood vessels that are diseased. Stents are generally hollow and cylindrical in shape and have terminal ends that are generally perpendicular to their longitudinal axis. In use, the conventional stent is positioned at the diseased area of a vessel and, after deployment, the stent provides an unobstructed pathway for blood flow.

Repair of vessels that are diseased at a bifurcation is particularly challenging since the stent must be precisely positioned, provide adequate coverage of the diseased area, provide access to any diseased area located distal to the bifurcation, and maintain vessel patency in order to allow adequate blood flow to reach the myocardium. Therefore, the stent must provide adequate coverage to the diseased portion of the bifurcated vessel, without compromising blood flow, and extend to a point within and beyond the diseased portion. Where the stent provides coverage to the vessel at the diseased portion, yet extends into the vessel lumen at the bifurcation, the diseased area is repaired, but blood flow may be compromised in other portions of the bifurcation. Unapposed stent elements may promote lumen compromise during neointimal formation and healing, producing restenosis and requiring further procedures. Moreover, by extending into the vessel lumen at the bifurcation, the stent may block access to further interventional procedures.

Conventional stents are designed to repair areas of blood vessels that are removed from bifurcations, and, therefore are associated with a variety of problems when attempting to use them to treat lesions at a bifurcation. Conventional stents are normally deployed so that the entire stent is either in the parent vessel or the proximal portion of the stent is in the parent vessel and the distal portion is located in the side branch vessel. In both cases, either the side branch vessel (former case) or the parent vessel (later case), would become "jailed" by the stent struts. This technique repairs one vessel at the bifurcation at the expense of jailing or obstructing the alternate vessel. Blood flow into the jailed vessel would be compromised as well as future access and treatment into the distal portion of the jailed vessel.

Alternatively, access into a jailed vessel can be attained by carefully placing a guide wire through the stent, and subsequently tracking a balloon catheter through the stent struts. The balloon could then be expanded, thereby deforming the stent struts and forming an opening into the previously jailed vessel. The cell to be spread apart must be randomly and blindly selected by recrossing the deployed stent with a guide wire. The drawback with this approach is that there is no way to determine or guarantee that the main vessel stent struts are properly oriented with respect to the side branch or that an appropriate stent cell has been selected by the wire for dilatation. The aperture created often does not provide a clear opening and creates a major distortion in the surrounding stent struts. A further drawback with this approach is that there is no way to tell if the main vessel stent struts have been properly oriented and spread apart to provide a clear opening for stenting the side branch vessel. This technique also causes stent deformation to occur in the area adjacent to the carina, pulling the stent away from the vessel wall and partially obstructing flow in the originally non jailed vessel. Deforming the stent struts to regain access into the previously jailed strut is also a complicated and time consuming procedure associated with attendant risks to the patient and is typically performed only if considered an absolute necessity. Vessels which supply a considerable amount of blood supply to the myocardium and may be responsible for the onset of angina or a myocardial infarction would necessitate the subsequent strut deformation in order to reestablish blood flow into the vessel. The risks of procedural complications during this subsequent deformation are considerably higher than stenting in normal vessels. The inability to place a guide wire through the jailed lumen in a timely fashion could restrict blood supply and begin to precipitate symptoms of angina or even cardiac arrest. In addition, platelet agitation and subsequent thrombus formation at the jailed site could further compromise blood flow into the side branch.

Plaque shift is also a phenomenon which is of concern when deploying a stent across a bifurcation. Plaque shift occurs when treatment of disease or plaque in one vessel causes the plaque to shift into another location. This is of greatest concern when the plaque is located on the carina or the apex of the bifurcation. During treatment of the disease the plaque may shift from one side of the carina to the other thereby shifting the obstruction from one vessel to the alternate vessel.

In another prior art method of implanting stents, a "T" stent procedure includes implanting a stent in the side branch ostium of the bifurcation followed by stenting the main vessel across the side branch and subsequently deforming the struts as previously described, to allow blood flow and access into the side branch vessel. Alternatively, a stent is deployed in the parent vessel and across the side branch origin followed by subsequent strut deformation as previously described, and finally a stent is placed into the side branch vessel. T stenting may be necessary in some situations in order to provide further treatment and additional stenting in the side branch vessel. This is typically necessitated when the disease is concentrated at the origin of the jailed vessel. This procedure is also associated with the same issues and risks previously described when stenting only one vessel and deforming the struts through the jailed vessel. In addition, since a conventional stent generally terminates at right angles to its longitudinal axis, the use of conventional stents to treat the origin of the previously jailed vessel (typically the side branch vessel) may result in blocking blood flow of the originally non-jailed vessel (typically the parent vessel) or fail to provide adequate coverage of the disease in the previously jailed vessel (typically a side branch vessel). The conventional stent might be placed proximally in order to provide full coverage around the entire circumference of the side branch, however this leads to a portion of the stent extending into the pathway of blood flow of the parent vessel. The conventional stent might alternatively be placed distally to, but not entirely overlaying the circumference of the origin of the side branch to the diseased portion. Such a position of the conventional stent results in a bifurcation that does not provide full coverage or has a gap on the proximal side (the origin of the side branch) of the vessel and is thus not completely repaired. The only conceivable situation that the conventional stent, having right angled terminal ends, could be placed where the entire circumference of the ostium is repaired without compromising blood flow, is where the bifurcation is formed of right angles.

In such scenarios, extremely precise positioning of the conventional stent is required. This extremely precise positioning of the conventional stent may result with the right angled terminal ends of the conventional stent overlying the entire circumference of the ostium to the diseased portion without extending into a side branch, thereby repairing the right angled bifurcation.

To circumvent or overcome the problems and limitations associated with conventional stents in the context of repairing diseased bifurcated vessels, a stent that consistently overlays most of the diseased area of the bifurcation and provides adequate access to distal disease without subjecting the patient to any undue risks may be employed. Such a stent would have the advantage of providing adequate coverage at the proximal edge of the origin of the side branch such that a conventional stent which terminates at right angles to its longitudinal axis can be deployed in the side branch or alternate vessel without leaving a significant gap at the origin of the side branch. In addition, such a stent would allow access to all portions of the bifurcated vessel should further interventional treatment be necessary.

In another prior art method for treating bifurcated vessels, commonly referred to as the "Culotte technique," the side branch vessel is first stented so that the stent protrudes into the main or parent vessel. A dilatation is then performed in the main or parent vessel to open and stretch the stent struts extending across the lumen from the side branch vessel. Thereafter, a stent is implanted in the side branch so that its proximal end overlaps with the parent vessel. One of the drawbacks of this approach is that the orientation of the stent elements protruding from the side branch vessel into the main vessel is completely random. In addition excessive metal coverage exists from overlapping strut elements in the parent vessel proximal to the carina area. Furthermore, the deployed stent must be recrossed with a wire blindly and arbitrarily selecting a particular stent cell. When dilating the main vessel the stent struts are randomly stretched, thereby leaving the possibility of restricted access, incomplete lumen dilatation, and major stent distortion.

In another prior art procedure, known as "kissing" stents, a stent is implanted in the main vessel with a side branch stent partially extending into the main vessel creating a double barreled lumen of the two stents in the main vessel distal to the bifurcation. Another prior art approach includes a so called "trouser legs and seat" approach, which includes implanting three stents, one stent in the side branch vessel, a second stent in a distal portion of the main vessel, and a third stent, or a proximal stent, in the main vessel just proximal to the bifurcation.

All of the foregoing stent deployment assemblies suffer from the same problems and limitations. Typically, there are uncovered intimal surface segments on the main vessel and side branch vessels between the stented segments or there is excessive coverage in the parent vessel proximal to the bifurcation. An uncovered flap or fold in the intima or plaque will invite a "snowplow" effect, representing a substantial risk for subacute thrombosis, and the increased risk of the development of restenosis. Further, where portions of the stent are left unapposed within the lumen, the risk for subacute thrombosis or the development of restenosis again is increased. The prior art stents and delivery assemblies for treating bifurcations are difficult to use and deliver making successful placement nearly impossible. Even where placement has been successful, the side branch vessel can be "jailed" or covered so that there is impaired access to the stented area for subsequent intervention. Further, even with the various patterns of the portal region of a currently manufactured type of bifurcated stent, there is a tendency of the ring or rings of the portal region to immediately overlap with an adjacent ring of the proximal section during stent deployment. The present invention solves these and other problems as will be shown.

SUMMARY OF THE INVENTION

The present invention provides for improved stent patterns for the portal region of a side branch access stent to prevent the occurrence of portal overlap during deployment of the stent. A method of making a stent for repairing a bifurcated vessel is further disclosed herein.

The stent of the present invention includes a cylindrical body having a proximal opening, a distal opening, and a central (portal) opening. The distal opening and the proximal opening are aligned along the stent longitudinal axis and typically would be implanted in the main vessel, while the central opening is radially offset relative to the alignment of the distal opening and the proximal opening. The stent is implanted so that the central opening provides access to the side branch (or alternative vessel) and the ring or rings proximal to the central opening provide support and coverage to the origin of the side branch and to the area immediately proximal to the carina. The cylindrical body of the stent includes a plurality of rings aligned along a longitudinal axis, where each ring has a delivery diameter in which it is crimped or compressed tightly onto the balloon catheter, and an implanted diameter where the stent is implanted in a bifurcated vessel. Each ring also includes a number of first peaks that are configured to spread apart to permit the rings to be greatly expanded outwardly or to be compressed radially inwardly onto the balloon portion of a delivery catheter.

In one embodiment, the cylindrical body includes a proximal section, a distal section, and a central section. The proximal section includes between one and fifteen rings, the distal section includes between one and fifteen rings, and the central section includes between one and ten rings. The number of first peaks in the central section differs from the number of first peaks in the proximal section and the distal section. The plurality of first peaks have a proximal end and distal end such that the proximal end of at least one first peak of the central section is connected to the distal end of at least one first peak of the proximal section by at least one link. A central opening of the distal section is adjacent to the proximal end of the at least one first peak of the central section connected to the distal end of the at least one first peak of the proximal section by the at least one link.

In another embodiment, the rings of the proximal section have between four and twelve first peaks, the rings of the distal section have between four and twelve first peaks, and the rings of the central section have between five and fifteen first peaks. In another embodiment of the stent, the rings of the proximal section have seven first peaks, the rings of the distal section have six first peaks, and the rings of the central section have eight first peaks. In each of the embodiments, the rings are connected by at least one link between adjacent rings. The links connecting the rings can have various embodiments including straight segments, curved segments, undulating segments, and non-linear segments.

In yet another embodiment, the number of first peaks in the rings of the central section is proportional to the number of links connecting the first peaks of the central section and proximal section.

In a further embodiment, the central section includes one ring having eight first peaks such that the proximal end of one first peak of the central section is connected to the distal end of one first peak of the proximal section by two links. In another embodiment, the central section includes one ring having eight first peaks such that the proximal end of two first peaks of the central section is each connected to the distal end of one first peak of the proximal section and to the distal end of one second peak of the proximal section by one link.

In another embodiment, the proximal end of the at least one first peak of the central section and the distal end of the at least one first peak of the proximal section are connected in an out of phase configuration.

The plurality of first peaks of the stent of the present invention are formed of struts having a length. In one embodiment, the length of the first peaks is inversely proportional to the length of the at least one link connecting the first peaks of the central section and the proximal section of the stent.

Each ring of the stent of the present invention has at least one second peak where at least some of the at least one second peaks are connected to a link.

The stent of the present invention includes struts that make up the rings and links, the struts having either uniform cross-section, or cross-sections having various widths and thicknesses.

In another embodiment, the stent of the present invention is coated with at least one layer of a therapeutic agent or drug. In such instance, at least a portion of the stent can be coated with a primer material, which adheres to the stent, the primer material being coated with at least one layer of a therapeutic agent or drug.

The present invention also provides for a method of making a stent for repairing a bifurcated vessel.

Other features and advantages of the invention will become apparent from the following detailed description taken in conjunction with the accompanying drawings, which illustrate, by way of example, the features of the invention.

BRIEF DESCRIPTION OF THE DRAWINGS

FIG. 19 is a flattened elevational view depicting one embodiment of the stent of the present invention.

FIG. 20 is a flattened elevational view depicting one embodiment of the stent of the present invention in which at least some of the links have an undulating portion.

FIG. 21B is a portion of the stent pattern of the present invention depicting struts of variable width.

DETAILED DESCRIPTION OF THE PREFERRED EMBODIMENTS

Figure 1:
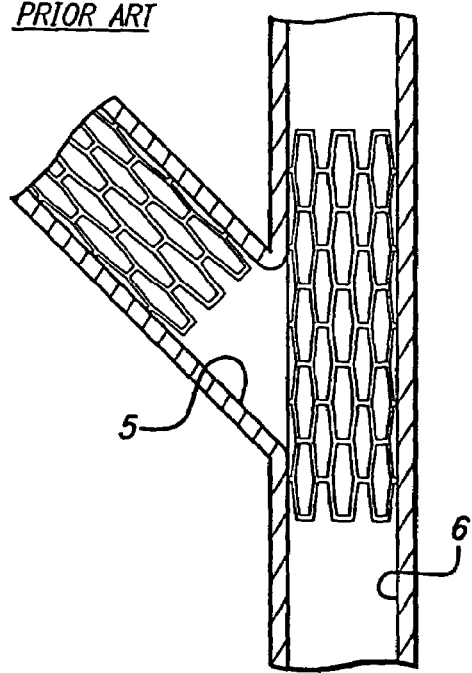
FIG. 1 is an elevational view of a bifurcation in which a prior art "T" stent is in a side branch ostium followed by the stenting of the main vessel across the branch ostium.

The present invention is directed to improved stent patterns for the portal region of a stent in the treatment of a bifurcation in the coronary arteries, veins, peripheral vessels, and other body lumens. Prior art attempts at implanting intravascular stents in a bifurcation have proved less than satisfactory. For example, FIGS. 1-4 depict prior art devices which include multiple stents being implanted in both the main vessel and a side branch vessel. In FIG. 1, a prior art "T" stent is implanted such that a first stent is implanted in the side branch near the origin of the bifurcation, and a second stent is implanted in the main vessel, into the side branch. With this approach, portions of the side branch vessel are left uncovered, and blood flow to the side branch vessel must necessarily pass through the main vessel stent, causing possible obstructions or thrombosis.

Figure 2:
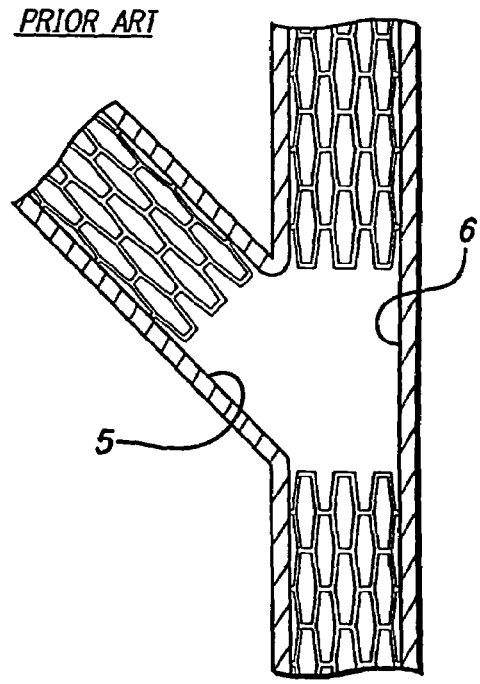
FIG. 2 is an elevational view of a bifurcation in which "touching" prior art stents are depicted in which one stent is implanted in the side branch, a second stent implanted in a proximal portion of the main vessel next to the branch stent, with interrupted placement of a third stent implanted more distally in the main vessel.
Figure 3:
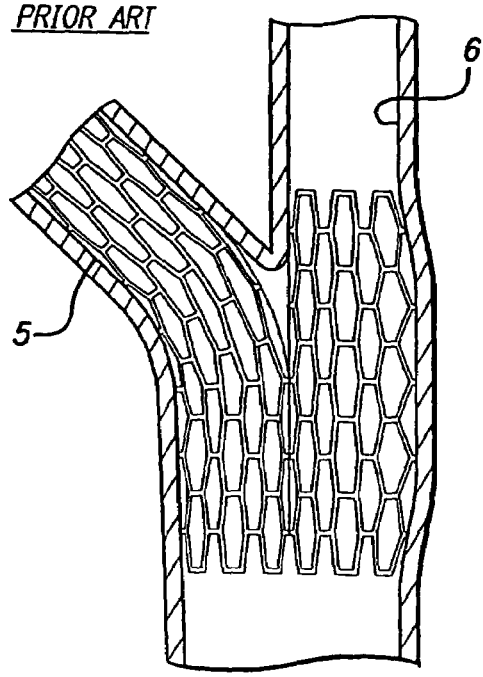
FIG. 3 is an elevational view of a bifurcation depicting "kissing" stents where a portion of one stent is implanted in both the side branch and the main vessel and adjacent to a second stent implanted in the main vessel creating a double-barreled lumen in the main vessel distal to the bifurcation.
Figure 4:
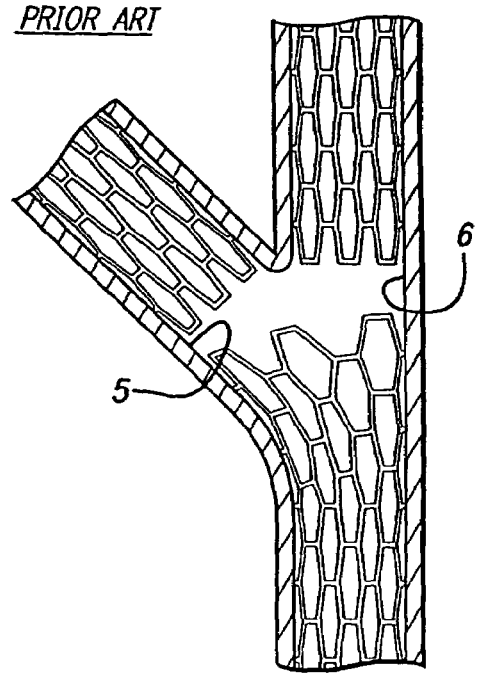
FIG. 4 is an elevational view of a prior art "trouser legs and seat" stenting approach depicting one stent implanted in the side branch vessel, a second stent implanted in a proximal portion of the main vessel, and a close deployment of a third stent distal to the bifurcation leaving a small gap between the three stents of an uncovered luminal area.

Referring to FIG. 2, three prior art stents are required to stent the bifurcation. In FIG. 3, the prior art method includes implanting two stents side by side, such that one stent extends into the side branch vessel and the main vessel, and the second stent is implanted in the main vessel. This results in a double barreled lumen which can present problems such as thrombosis and turbulence in blood flow. Referring to the FIG. 4 prior art device, a first stent is implanted in the side branch vessel, a second stent is implanted in a proximal portion of the main vessel, and a third stent is implanted distal to the bifurcation, thereby leaving a small gap between the stents and an uncovered luminal area.

Figure 5A:
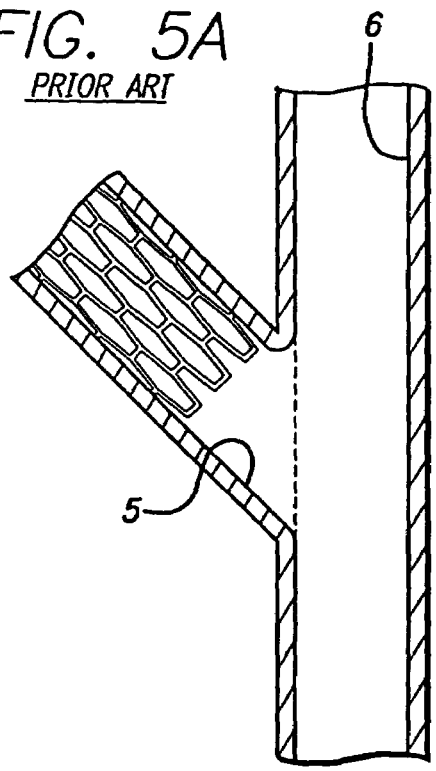
FIG. 5A is an elevational view of a bifurcation in which a prior art stent is implanted in the side branch vessel.
Figure 5B:
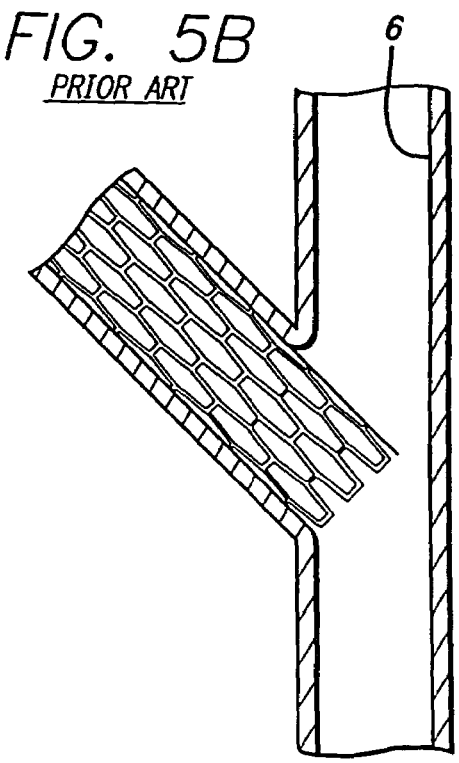
FIG. 5B is an elevational view of a bifurcation in which a prior art stent is implanted in the side branch vessel with the proximal end of the stent extending into the main vessel.

In treating side branch vessel 5, if a prior art stent is used in which there is no acute angle at the proximal end of the stent to match the angle of the bifurcation, a condition as depicted in FIGS. 5A and 5B will occur. That is, a stent deployed in side branch vessel 5 will leave a portion of the side branch vessel exposed, or as depicted in FIG. 5B, a portion of the stent will extend into main vessel 6.

The stent of the present invention can be implanted in the main or side branch vessels to treat a number of disease configurations at a bifurcation including, but not limited to, the following:

1. Treatment of a parent or main vessel and the origin of the side branch at a bifurcation with any angle associated between the side branch and parent vessel.

2. Treatment of a parent vessel proximal to the carina and the side branch vessel simultaneously.

3. Treatment of the proximal vessel extending only into the origin of the side branch and the origin of the distal parent at the bifurcation.

4. Treatment of the area at the bifurcation only.

5. The origin of an angulated posterior descending artery.

6. The origin of an LV extension branch just at and beyond the crux, sparing the posterior descending artery.

7. The origin of a diagonal from the left anterior descending.

8. The left anterior descending at, just proximal to, or just distal to the diagonal origin.

9. The origin of a marginal branch of the circumflex.

10. The circumflex at, just proximal to, or just distal to the marginal origin.

11. The origin of the left anterior descending from the left main.

12. The origin of the circumflex from the left main.

13. The left main at or just proximal to its bifurcation.

14. Any of many of the above locations in conjunction with involvement of the bifurcation and an alternate vessel.

15. Any bifurcated vessels within the body where conventional stenting would be considered a therapeutic means of treatment proximal or distal to the bifurcation.

Figure 6:
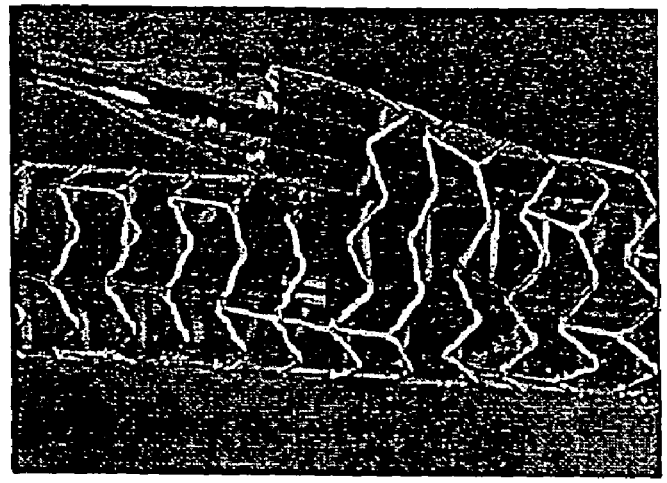
FIG. 6 is a photograph depicting the proper deployment (in air) of the Multi-Link Frontier™ Side Branch Access Coronary Stent.
Figure 7:
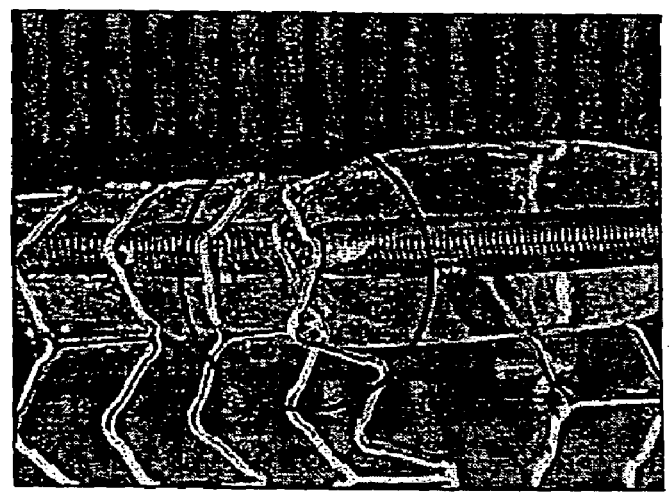
FIG. 7 is a photograph depicting the occurrence of portal overlap during stent deployment.
Figure 8:
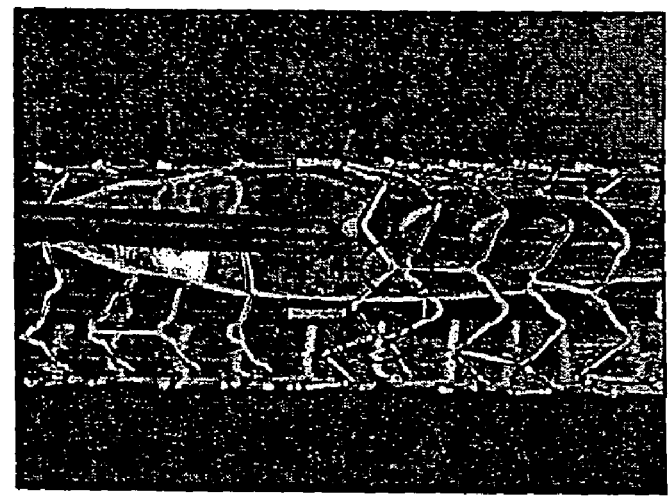
FIG. 8 is a photograph depicting the improved stent pattern of the stent of the present invention in preventing portal overlap.
Figure 9:
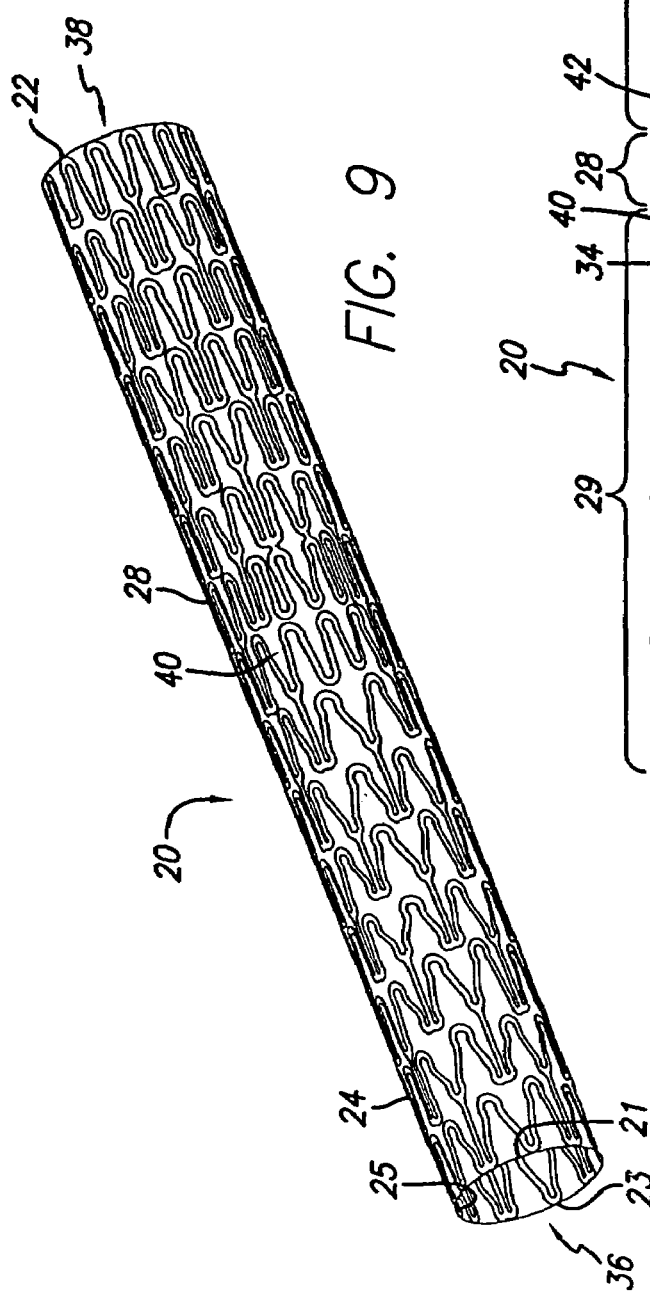
FIG. 9 is a perspective view depicting one embodiment of the stent of the present invention in an unexpanded configuration.
Figure 10:
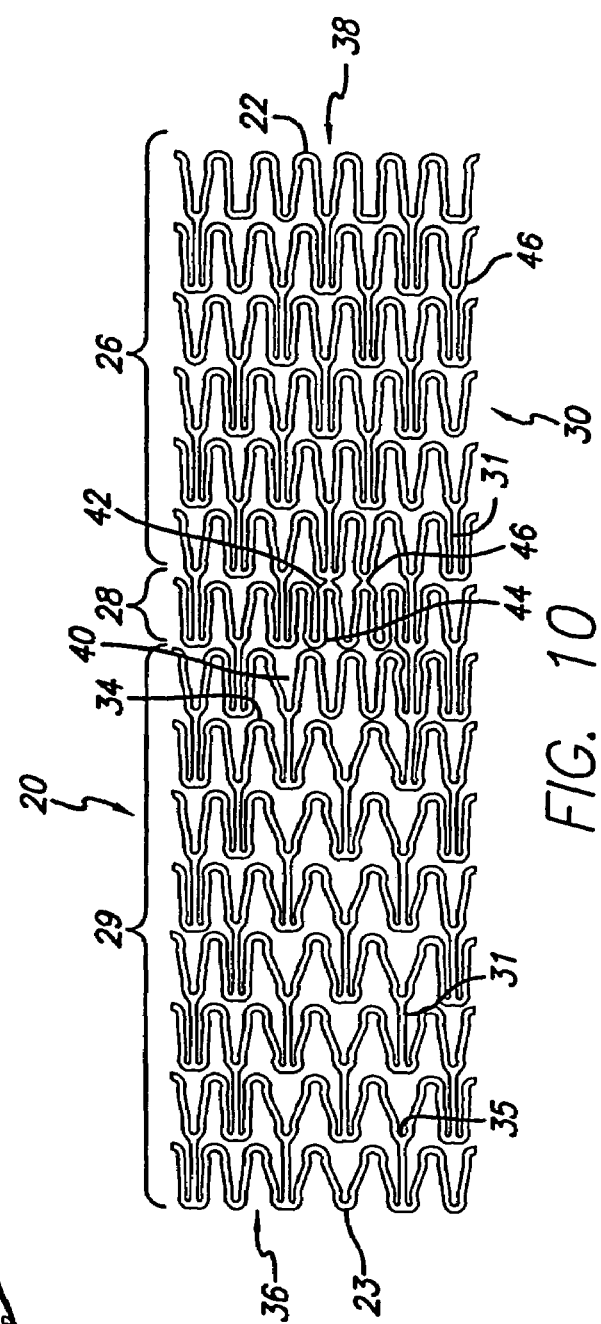
FIG. 10 is a flattened elevational view of the stent of FIG. 9, depicting one embodiment of the stent of the present invention.
Figure 11:
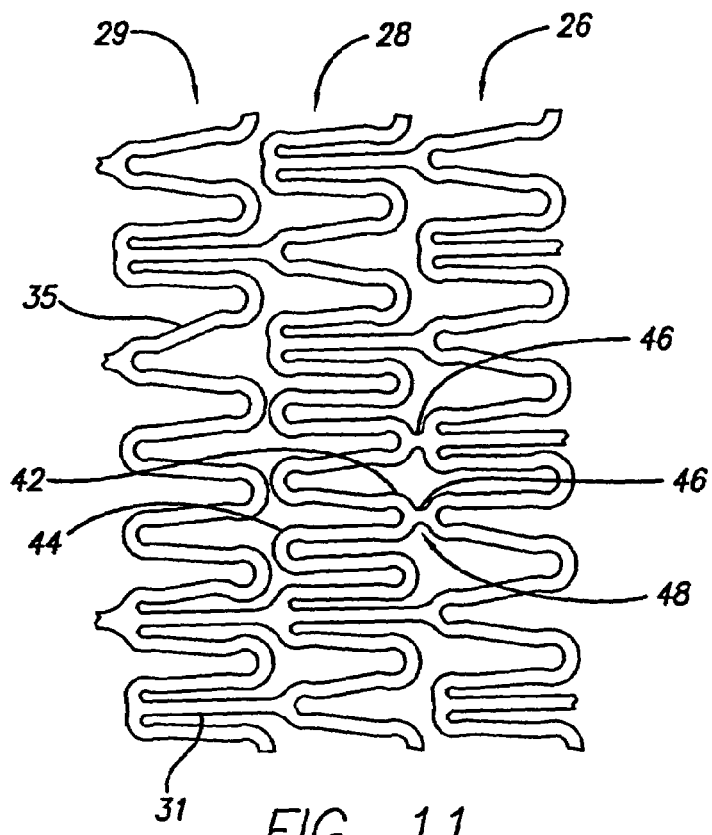
FIG. 11 is an enlarged view of a central (portal) section of the stent of the present invention depicted in FIG. 10.

The present invention stent is an improvement over an existing stent specifically designed for treating bifurcations, known as the Multi-Link Frontier™ Side Branch Access Coronary Stent ("Frontier™ stent"), manufactured by Advanced Cardiovascular Systems, Inc. of Santa Clara, Calif. Each of the prior art devices depicted in FIGS. 1-5 has various drawbacks, which have been solved by the Frontier™ stent. The Frontier™ stent adequately covers the main branch vessel and extends partially into the side branch vessel to cover the origin of the side branch vessel as well. The present invention includes an improved stent pattern for the portal region of the Frontier™ stent to prevent the occurrence of portal overlap. The condition of portal overlap may be characterized as the overlap of the proximal end ring of the portal region onto an adjacent ring of the proximal section during stent deployment in which the proximal end ring either remains overlapped after deflation of balloon or slides forward again. As shown in FIG. 6, the Frontier™ stent is properly deployed (shown in air as opposed to in the body lumen) when all of the rings 30 are fully expanded with no overlapping of the rings in the proximal section of the portal region onto adjacent rings. Previous studies have indicated that on some occasions, typically with larger bifurcated angles, the portal region of a bifurcated stent, such as the Frontier™ stent, is susceptible to portal overlap (affected area enclosed within circle), as shown in FIG. 7. The bifurcated stent of the present invention solves the problem of portal overlap with the addition of at least one link connecting the proximal end of at least one first peak of the central section with the distal end of at least one first peak of the proximal section, as will be set forth in further detail below. As shown in FIG. 8, the incorporation of the at least one link (shown encircled) into the stent design of the portal region of the present invention stent enhances the full expansion of the stent and prevents the onset of portal overlap.

The stent pattern of the present invention is novel in that it provides for vessel wall coverage of the main branch vessel and at least partial coverage of the origin of the side branch vessel. More specifically, in FIGS. 9-21, several embodiments of the bifurcated stent 20 having an improved portal region 28 are shown. The bifurcated stent can be characterized as a "trap door" since the stent pattern is configured so that as the stent is expanded, a central portion of the stent flares radially outwardly and opens to a greater diameter than the remainder of the stent, like a trap door, seemingly hidden until opened. The trap door portion, as will be further described herein, expands or opens to cover the opening to the side branch vessel. The terms "trap door," "portal," and "central section" may be used interchangeably herein. Once stent 20 is implanted in the main branch vessel and the opening to the side branch vessel, a second, conventional stent can be implanted in the side branch vessel, essentially abutting the trap door portion of the stent.

The bifurcated stent 20 of the present invention may be referred to as a "trap door" stent since the central portion of the stent is somewhat hidden during delivery and opens like a trap door to treat a bifurcated vessel when the stent is expanded. The stent of the present invention has a cylindrical body 21 that includes a proximal end 22 and a distal end 23. The stent has an outer surface 24 which contacts the vascular wall when implanted and an inner surface 25 through which blood flows when the stent is expanded and implanted. The stent can be described as having numerous connected rings 30 aligned along a common longitudinal axis of the stent. The rings are formed of undulating portions which include first peaks 34 that are configured to be spread apart to permit the stent to be expanded to a larger diameter or compressed tightly toward each other to a smaller diameter onto a catheter. The rings are connected to each other by at least one link 31 between adjacent rings so that the rings are in an in phase configuration (rings point in the same direction). Typically, there are three links that connect adjacent rings and the links of one ring are circumferentially offset by about 60° from the links of an adjacent ring. While the links 31 typically are offset as indicated, this is not always the case, especially in the area of the trap door. The number of links between adjacent rings does vary, however, in view of the trap door configuration.

The cylindrical body of the stent has a proximal section 26, a distal section 29 and a central section 28 where the proximal section can have between one and fifteen rings 30, the distal section can have between one and fifteen rings, and the central section will have between one and ten rings. The number of first peaks 34 in the central section generally will differ from the number of first peaks 34 in the proximal section and the distal section.

The central-section 28 is essentially the trap door portion of the stent and is enlarged to appose the entrance to the side branch vessel when the stent is expanded. As used herein, "appose" means that the expanded stent comes into contact with the vessel or artery wall. By way of example, in one embodiment shown in FIGS. 9-11, the rings 30 of the proximal section 26 have seven first peaks, the rings of the distal section 29 have six first peaks, and the rings of the central section 28 have eight first peaks. Each of the rings has at least one second peak 35, which is connected to link 31. A plurality of first peaks 34 having a proximal end 42 and a distal end 44 is configured so that the proximal end of two first peaks of the central section is each connected to the distal end of one first peak of the proximal section and to the distal end of one second peak of the proximal section by two separate links 46 resulting in a peak-to-peak or out of phase (peaks point toward each other) configuration 48. Thus, when expanded, the ring or rings of the central section will expand and the first and second peaks will spread apart to appose (contact) the entrance to the side branch vessel. The remainder of the rings in the proximal section are connected in a peak-to-valley or in phase configuration (peaks point in the same direction). This same peak-to-valley or in phase configuration is present with respect to each of the rings in the distal section of the stent. The rings of the proximal section and distal section will expand into apposition with the walls of the main branch vessel. Due to this unique configuration of incorporating at least one additional link into the stent pattern of the central section and connecting such link to an immediately adjacent ring on the distal end of the proximal section so that the respective adjacent rings are in a peak-to-peak configuration, the onset of portal overlap is effectively avoided. The number of peaks per section is a matter of choice depending upon the application and the type of bifurcated vessel to be treated. The peaks are spaced on the rings in such a fashion as to provide uniformity after final expansion, since a bifurcated stent does not necessarily expand coaxially inside the vessel.

Figure 12:
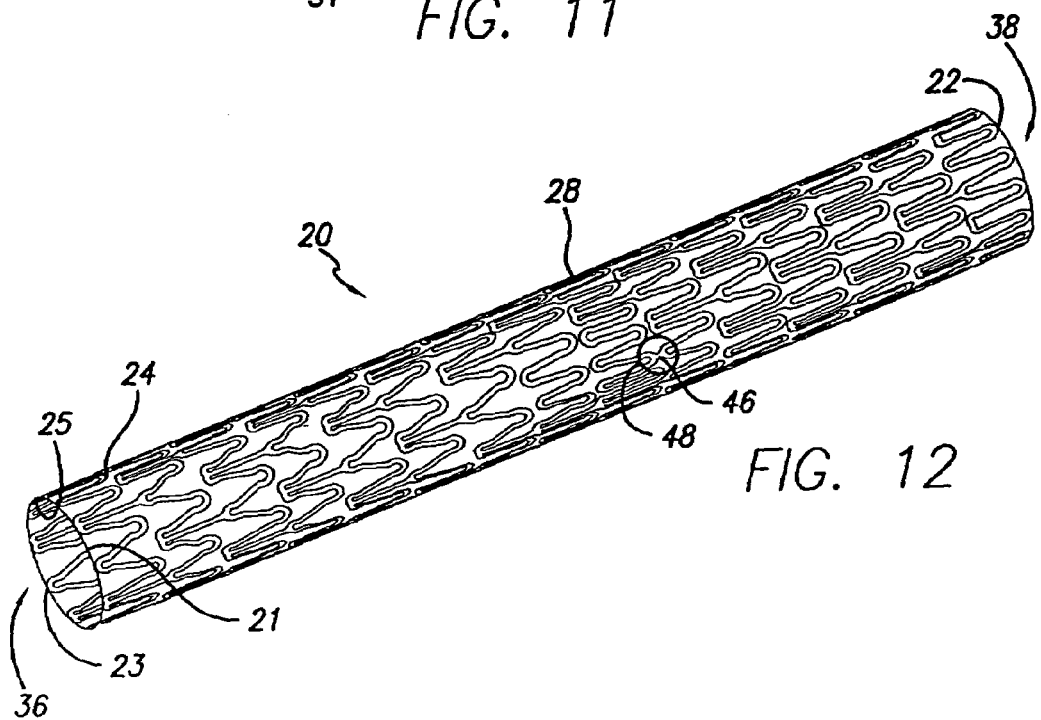
FIG. 12 is a perspective view depicting one embodiment of the stent of the present invention in an unexpanded configuration.
Figure 13:
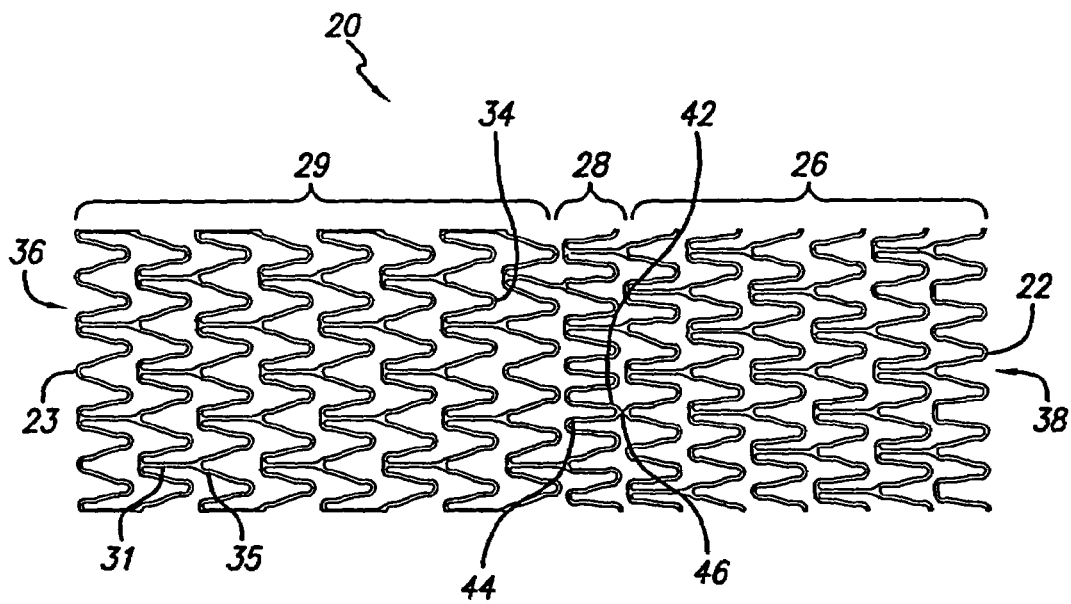
FIG. 13 is a flattened elevational view of the stent of FIG. 12, depicting one embodiment of the stent of the present invention.
Figure 14:
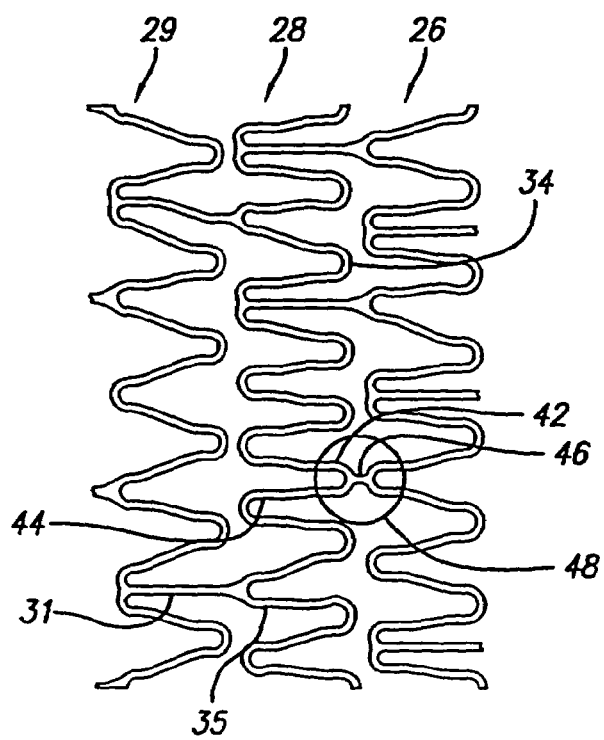
FIG. 14 is an enlarged view of the central (portal) section of the stent of the present invention depicted in FIG. 13.

FIGS. 12-14 illustrate another embodiment of the present invention stent in which there is only one peak-to-peak configuration 48 incorporated into the pattern of the stent central section 28. In this embodiment, the first peak proximal end 42 of the central section 28 is connected to the first peak distal end 44 of the proximal section 26 by one link 46. As in the previous embodiment, when expanded, the ring or rings of the central section will expand and the first peaks will spread apart to appose (contact) the entrance to the side branch vessel. The rings of the proximal section and the distal section will expand into contact with the walls of the main branch vessel. Further, the remainder of the rings in the proximal section are connected in a peak-to-valley or in phase configuration. This same peak-to-valley or in phase configuration is present with respect to each of the rings in the distal section of the stent. At least one ring of the central section is connected to at least one adjacent ring of at least one of the proximal section and the distal section in an in phase configuration.

A central opening 40 in the distal section 29 of the stent allows the passage of a balloon contained on the delivery system. The stent is to be crimped tightly onto two separate expandable members of a catheter. Typically, the expandable portions of the catheter will be balloons similar to a dilatation type balloon for conventional dilatation catheters. In the present invention, the bifurcated stent 20 is configured such that the stent has a distal opening 36 and a proximal opening 38 that are in axial alignment and through which a longer balloon extends, and the central opening 40 which is adjacent the central section 28 or "trap door," through which a shorter balloon extends. The stent can be crimped tightly onto both the long and short balloons. In this embodiment, the central opening of the distal section is adjacent to the proximal end 42 of one first peak of the central section connected to the distal end 44 of one first peak of the proximal section by link 46.

Figure 15:
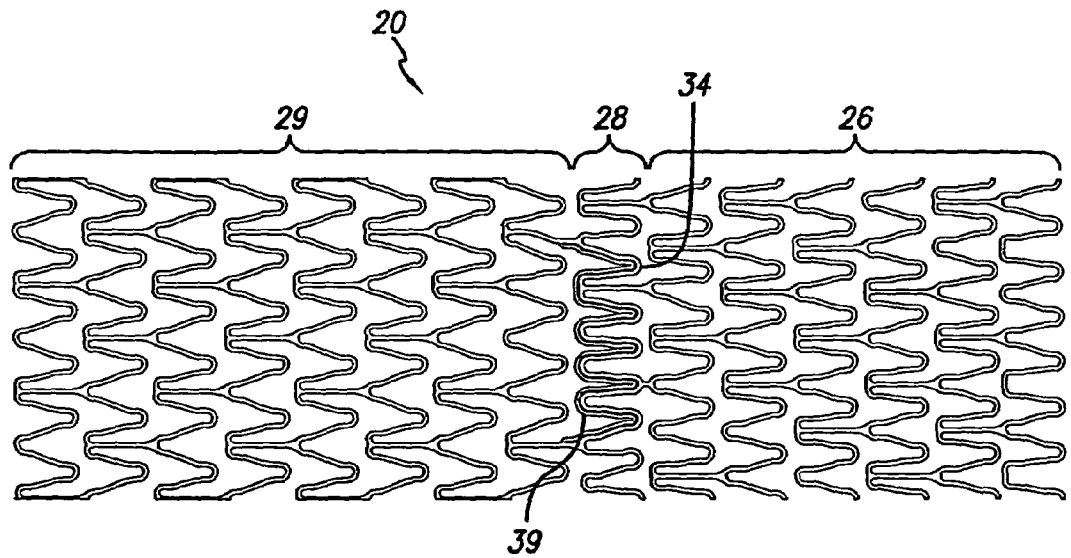
FIG. 15 is a flattened elevational view of one embodiment of the stent of the present invention.
Figure 16:
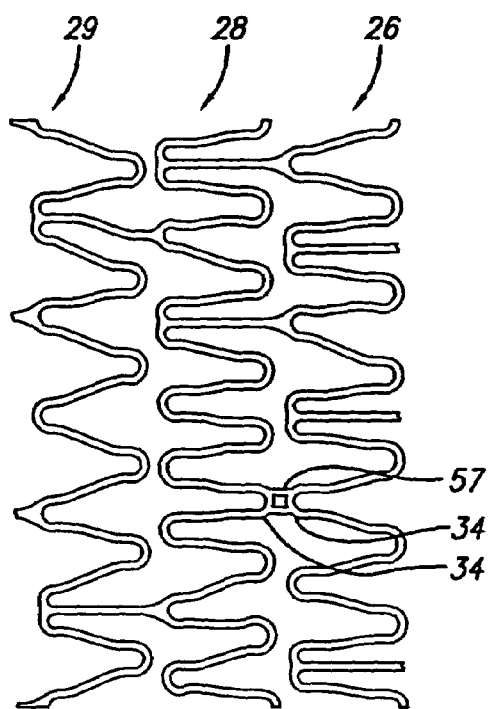
FIG. 16 is a flattened elevational view depicting one embodiment of the stent of the present invention.
Figure 17:
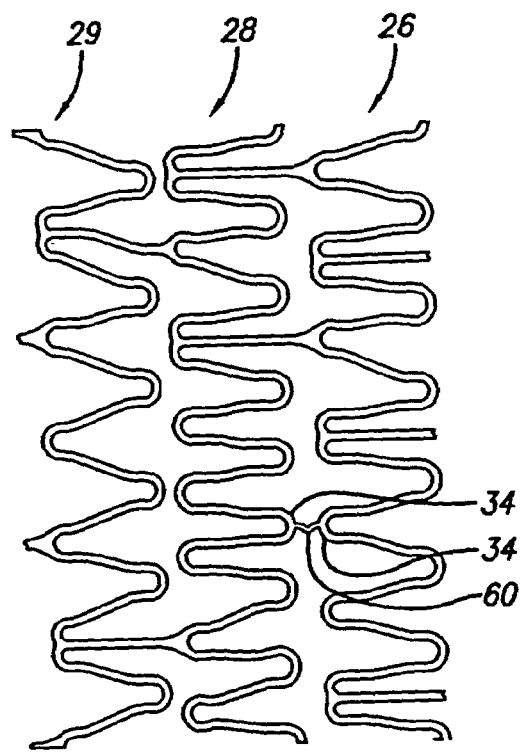
FIG. 17 is a flattened elevational view depicting one embodiment of the stent of the present invention.
Figure 18:
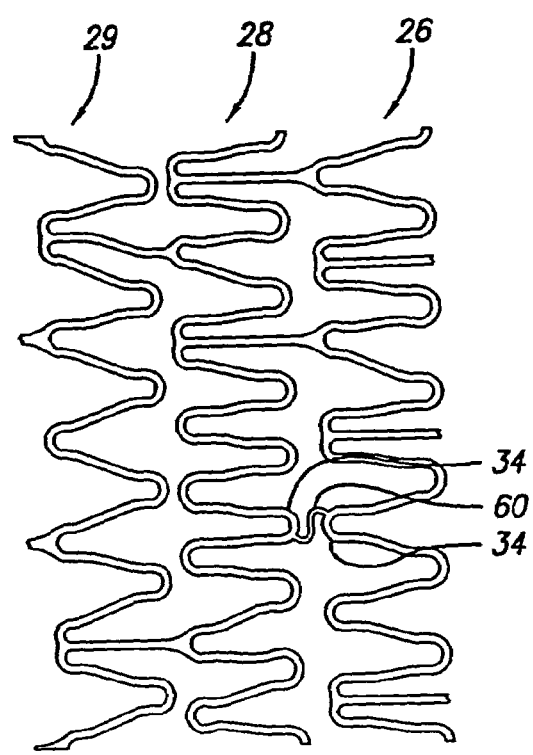
FIG. 18 is a flattened elevational view depicting one embodiment of the stent of the present invention.

In another embodiment shown in FIG. 15, the ring 30 or rings in the central section 28 of the stent 20 have a corresponding set of nested peaks 39 nested within the first peaks 34 of the ring or rings of the central section. The nested peaks, when expanded, will appose the opening to the side branch vessel and provide additional support as well as vessel wall coverage. With the addition of the nested peaks, the central section can expand to an even greater diameter than a similar stent without the nested peaks because the extra peaks provide more material to expand.

It is contemplated by the present invention that the at least one link 46 connecting one first peak 34 of the central section 28 to an adjacent first peak 34 of the proximal section 26 can be of various shapes and sizes, including standard straight links 57, long straight links 58, and non-linear links 60 having curved portions. In one embodiment shown in FIG. 16, two separate straight links 57 connect one first peak of the central section to the adjacent first peak of the proximal section in the characteristic peak-to-peak configuration 48 of the present invention bifurcated stent 20. In other embodiments shown in FIGS. 17-18, the link connecting the one first peak 34 of the central section 28 to the adjacent first peak 34 of the proximal section 26 may be configured as a non-linear link 60 having curved portions.

In a further embodiment shown in FIG. 19, the length of the first peaks 34 is inversely proportional to the length of the at least one link 62 that connects the first peaks of the central section 28 and the proximal section 26 in a peak-to-peak configuration 48. For example, the central section of the stent includes first peaks 34 and second peaks 35 having a strut length that is proportionately shorter than the length of link 62.

With all of the embodiments of the bifurcated stent 20 disclosed herein, the rings 30 can be attached to each other by links 31 having various shapes, including straight links 32 or non linear links 33 having curved portions. The non linear links, as shown in FIG. 20, can have undulating portions 37 that are perpendicular (or offset) to the longitudinal axis of the stent and act as a hinge to enhance the flexibility of the stent. The links are not limited by any particular length or shape and can be a weld, laser fusion, or similar connection. Welds or laser fusion processes are particularly suited to stent patterns that are out of phase (peaks point toward each other) as opposed to the in phase pattern (peaks point in the same direction) shown in the drawings. Furthermore, with all of the embodiments of the bifurcated stent 20, the stent can be used to treat coronary arteries having vulnerable plaque.

Figure 21A:
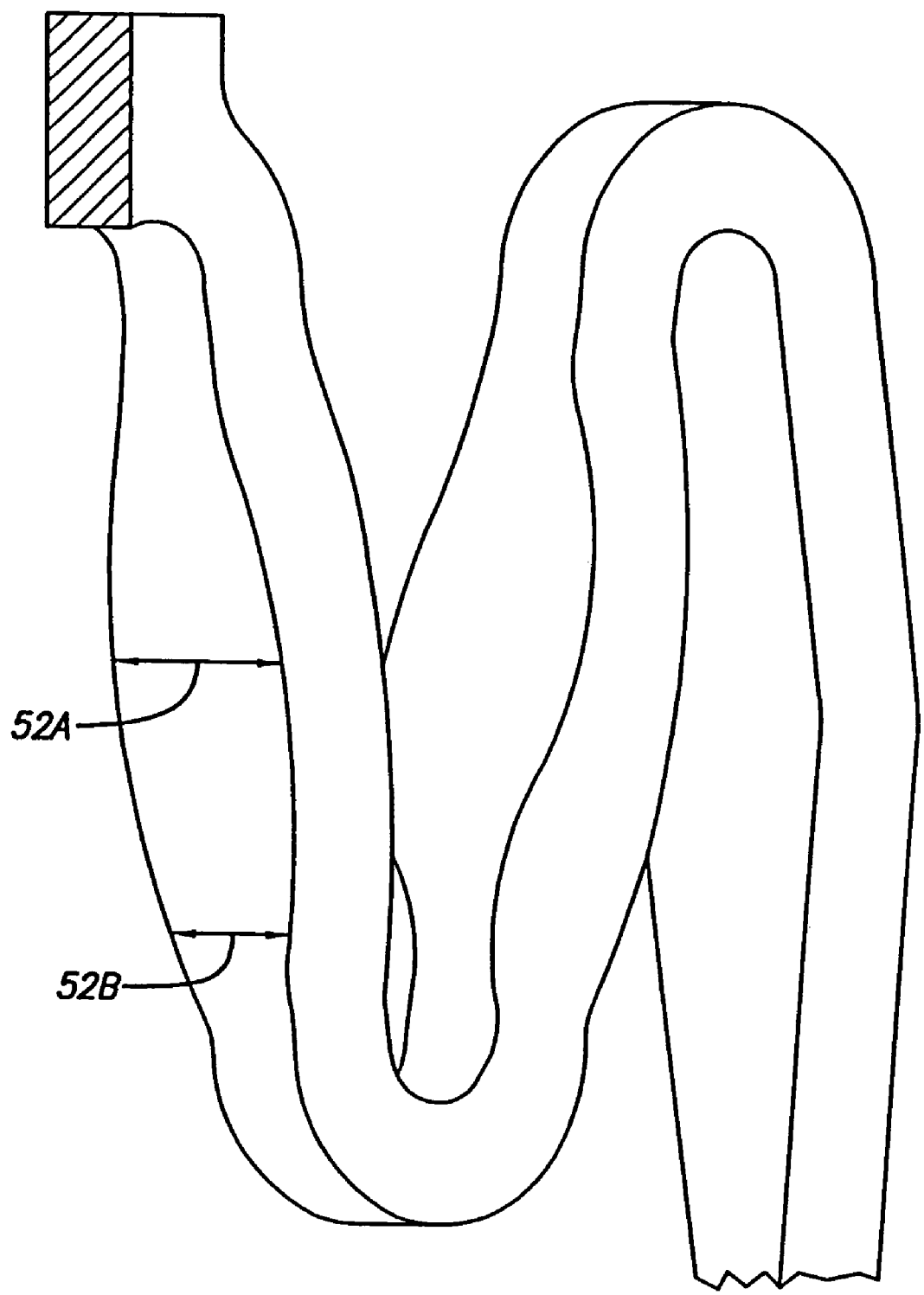
FIG. 21A is a portion of the stent pattern of the present invention depicting struts of variable thickness.

Each embodiment of the stent 20 also can have rings 30 and links 31 that have variable thickness struts 52A and 52B, as shown in FIG. 21A, at various points in order to increase the radial strength of the stent, provide higher radiopacity so that the stent is more visible under fluoroscopy, and enhance flexibility in the portions where the stent has the thinnest struts. The stent also can have variable width struts 54A and 54B, as shown in FIG. 21B, to vary flexibility, maximize vessel wall coverage at specific points, or to enhance the stent radiopacity. The variable thickness struts or variable width struts, which may be more radiopaque than other struts, can be positioned along the stent to help the physician position the stent during delivery and implantation in the bifurcated vessel.

The bifurcated stent 20 can be formed in a conventional manner typically by laser cutting a tubular member or by laser cutting a pattern (as in one of the embodiments disclosed herein) into a flat sheet, rolling it into a cylindrical body, and laser welding a longitudinal seam along the longitudinal edges of the stent. The stent can also be fabricated using conventional lithographic and etching techniques where a mask is applied to a tube or flat sheet. The mask is in the shape of the final stent pattern and is used for the purpose of protecting the tubing during a chemical etching process which removes material from unwanted areas. Electro discharge machining (EDM) can also be used for fabricating the stent, where a mold is made in the negative shape of the stent and is used to remove unwanted material by use of an electric discharge. The method of making stents using laser cutting processes or the other described processes are well known in the art. The stent of the invention typically is made from a metal alloy and includes any of stainless steel, titanium, nickel titanium (NiTi or nitinol of the shape memory or superelastic types), tantalum, cobalt chromium, cobalt chromium vanadium, cobalt chromium tungsten, gold, silver, platinum, platinum iridium or any combination of the foregoing metals and metal alloys. Any of the listed metals and metal alloys can be coated with a polymer containing fluorine 19 ($^{19}$F) used as a marker which is visible under magnetic resonance imaging (MRI). Portions of the stent, for example some of the links, can be formed of a polymer impregnated with $^{19}$F so that the stent is visible under MRI. Other compounds also are known in the art to be visible under MRI and can be used in combination with the disclosed metal stent of the invention.

The stent of the invention also can be coated with a drug or therapeutic agent to assist in repair of the bifurcated vessel and may be useful, for example, in reducing the likelihood of the development of restenosis. Further, it is well known that the stent (usually made from a metal) may require a primer material coating to provide a substrate on which a drug or therapeutic agent is coated since some drugs and therapeutic agents do not readily adhere to a metallic surface. The drug or therapeutic agent can be combined with a coating or other medium used for controlled release rates of the drug or therapeutic agent. Examples of therapeutic agents or drugs that are suitable for use in accordance with the present invention include 17-beta estradiol, sirolimus, everolimus, actinomycin D (ActD), taxol, paclitaxel, or derivatives and analogs thereof. Examples of agents include other antiproliferative substances as well as antineoplastic, antiinflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents include antiplatelets, anticoagulants, antifibrins, antiinflammatories, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B® (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from Hoffman-LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck), methotrexate, monoclonal antibodies (such as PDGF receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agents is known in the art. The calculation of dosages, dosage rates and appropriate duration of treatment are previously known in the art. Furthermore, the therapeutic drugs or agents are loaded at desired concentration levels per methods well known in the art to render the device ready for implantation.

It should be understood that any reference in the specification or claims to a drug or therapeutic agent being coated on the stent is meant that one or more layers can be coated either directly on the stent or onto a primer material on the stent to which the drug or therapeutic agent readily attaches.

While particular forms of the invention have been illustrated and described, it will be apparent to those skilled in the art that various modifications can be made without departing from the scope of the invention. Accordingly, it is not intended that the invention be limited except as by the appended claims.

What is claimed:

1. A stent for repairing a bifurcated vessel, comprising:
a cylindrical body having a plurality of rings aligned along a common longitudinal axis;
each ring having a delivery diameter and an implanted diameter and a plurality of peaks configured to spread apart to permit the rings to expand radially outwardly or compress radially inwardly;
the cylindrical body having a proximal section, a distal section, and a central section;
each ring being connected to each adjacent ring by at least one link extending between peaks wherein such peaks point in a same direction; and
at least one peak of a central section ring being connected to at least one peak of a proximal section ring by at least one link wherein the connected peaks point toward each other, and at least one peak in every ring is not connected to any peak in an adjacent ring.

2. The stent of claim 1, wherein the rings of the proximal section have between eight and twenty four peaks, the rings of the distal section have between eight and twenty four peaks, and the rings of the central section have between ten and thirty peaks.

3. The stent of claim 1, wherein the rings of the proximal section have fourteen peaks, the rings of the distal section have twelve peaks, and the rings of the central section have sixteen peaks.

4. The stent of claim 1, wherein the number of peaks in the ring(s) of the central section is greater than the number of peaks in any of the rings in either the proximal section or the distal section.

5. The stent of claim 1, wherein at least some of the links have a straight segment.

6. The stent of claim 1, wherein at least some of the links have a curved segment.

7. The stent of claim 1, wherein at least some of the links have a straight segment and a curved segment.

8. The stent of claim 1, wherein at least some of the links have a non-linear segment.

9. The stent of claim 1, wherein the cylindrical body has a distal opening, a proximal opening, and a central opening.

10. The stent of claim 9, wherein the distal opening and the proximal opening are aligned along the stent longitudinal axis.

11. The stent of claim 10, wherein the central opening is radially offset relative to the alignment of the distal opening and the proximal opening.

12. The stent of claim 1, wherein the stent is formed from metal.

13. The stent of claim 12, wherein the metal is taken from the group of metals including stainless steel, titanium, nickel-titanium, cobalt-chromium, cobalt-chromium-vanadium, cobalt-chromium-tungsten, gold, silver, platinum, or platinum-iridium.

14. The stent of claim 1, wherein the at least one link has a thickness in the range from about 0.001 inch (0.025 mm) up to about 0.006 inch (0.152 mm).

15. The stent of claim 1, wherein the at least one link has a width in the range from about 0.001 inch (0.025 mm) up to about 0.006 inch (0.152 mm).

16. The stent of claim 1, wherein the at least one link has a straight segment.

17. The stent of claim 1, wherein the at least one link has a curved segment.

18. The stent of claim 1, wherein the at least one link has a straight segment and a curved segment.

19. The stent of claim 1, wherein the at least one link has a non-linear segment.

20. The stent of claim 1, wherein the central section includes one ring having sixteen peaks such that one peak of the central section is connected to one peak of the proximal section by two links.

21. The stent of claim 1, wherein the ring or rings in the central section of the stent have a corresponding set of nested peaks within peaks of the ring or rings of the central section.

22. The stent of claim 1, wherein the stent is coated with at least one layer of a drug.

23. The stent of claim 1, wherein the stent is coated with at least one layer of a therapeutic agent.

24. The stent of claim 1, wherein at least a portion of the stent is coated with a primer material, which adheres to the stent, the primer material being coated with at least one layer of a therapeutic agent or drug.

25. The stent of claim 1, wherein the plurality of first peaks in the central section differing from the plurality of first peaks in the proximal section and the distal section.

26. A stent for repairing a bifurcated vessel, comprising:
a cylindrical body having a plurality of rings aligned along a common longitudinal axis;
each ring having a delivery diameter and an implanted diameter and a plurality of first peaks configured to spread apart to permit the rings to expand radially outwardly or compress radially inwardly;
the cylindrical body having a proximal section, a distal section, and a central section;
at least one first peak of the central section being connected to at least one first peak of the proximal section by at least one link wherein the connected first peaks point toward each other, and at least one first peak in every ring is not connected to any first peak in an adjacent ring; and
wherein a central opening of the distal section is adjacent to the at least one first peak of the central section that is connected to the at least one first peak of the proximal section by the at least one link.

27. The stent of claim 26, wherein two first peaks of the central section are each connected to one first peak of the proximal section and to one second peak of the proximal section by one link in an out of phase configuration.

28. The stent of claim 26, wherein at least one ring of the proximal section is connected to an adjacent ring of the proximal section in an in phase configuration.

29. The stent of claim 26, wherein at least one ring of the distal section is connected to at least one adjacent ring of the distal section in an in phase configuration.

30. The stent of claim 26, wherein at least one ring of the central section is connected to at least one adjacent ring of at least one of the proximal section and the distal section in an in phase configuration.

31. A stent for repairing a bifurcated vessel, comprising:
a cylindrical body having a plurality of rings aligned along a common longitudinal axis;
each ring having a delivery diameter and an implanted diameter and a plurality of first peaks configured to spread apart to permit the rings to expand radially outwardly or compress radially inwardly;
the cylindrical body having a proximal section, a distal section, and a central section;
the proximal section having between one and fifteen rings;
the distal section having between one and fifteen rings;
the central section having between one and ten rings;
the central section having an expanded diameter greater than the expanded diameter of the proximal section and the distal section; and
at least one first peak of the central section is connected to at least one first peak of the proximal section by at least one link wherein the connected first peaks point toward each other, and at least one first peak of any one ring is not connected to any first peak of an adjacent ring.

32. A stent for repairing a bifurcated vessel, comprising:
a cylindrical body having a plurality of rings aligned along a common longitudinal axis;
each ring having a delivery diameter and an implanted diameter and a plurality of first peaks configured to spread apart to permit the rings to expand radially outwardly or compress radially inwardly;
the cylindrical body having a proximal section, a distal section, and a central section;
means for connecting the plurality of first peaks so that at least one first peak of the central section is connected to at least one first peak of the proximal section wherein the connected first peaks point toward each other, and at least one first peak of any one ring is not connected to any first peak of an adjacent ring.

33. The stent of claim 32, wherein the means for connecting the plurality of first peaks is at least one link.

* * * * *

UNITED STATES PATENT AND TRADEMARK OFFICE
CERTIFICATE OF CORRECTION

| | | |
|---|---|---|
| PATENT NO. | : 7,465,315 B2 | Page 1 of 1 |
| APPLICATION NO. | : 11/495081 | |
| DATED | : December 16, 2008 | |
| INVENTOR(S) | : Grayson Morris et al. | |

It is certified that error appears in the above-identified patent and that said Letters Patent is hereby corrected as shown below:

Title Page, insert --Related U.S. Application Data
(60) Continuation of application No. 10/718,105, filed on Nov. 19, 2003, now Pat. No. 7,090,694--.

Signed and Sealed this

Twenty-first Day of April, 2009

JOHN DOLL
*Acting Director of the United States Patent and Trademark Office*